United States Patent [19]

Axelgaard

[11] 4,408,609

[45] Oct. 11, 1983

[54] ELECTRICAL MUSCLE STIMULATION FOR TREATMENT OF SCOLIOSIS AND OTHER SPINAL DEFORMITIES

[75] Inventor: Jens Axelgaard, Downey, Calif.

[73] Assignee: Professional Staff Association of the Rancho Los Amigos Hospital, Inc., Downey, Calif.

[21] Appl. No.: 343,485

[22] Filed: Jan. 28, 1982

Related U.S. Application Data

[62] Division of Ser. No. 136,310, Apr. 1, 1980, Pat. No. 4,342,317.

[51] Int. Cl.³ .............................................. A61N 1/36
[52] U.S. Cl. .................................................... 128/421
[58] Field of Search ............... 128/419 R, 420 R, 421, 128/422, 423 R

[56] References Cited

U.S. PATENT DOCUMENTS

| | | | |
|---|---|---|---|
| 3,077,884 | 2/1963 | Batrow et al. | 128/423 |
| 3,888,261 | 6/1975 | Maurer | 128/420 R |
| 3,893,463 | 7/1975 | Williams | 128/421 |
| 4,077,819 | 12/1979 | Kofsky et al. | 128/422 |

Primary Examiner—William E. Kamm
Attorney, Agent, or Firm—I. Morley Drucker

[57] ABSTRACT

Apparatus for correction of spinal curvature deficiencies such as scoliosis, lordosis, kyphosis and combinations thereof, utilizing transcutaneous, percutaneous or subcutaneous electrical muscle stimulation of certain target musculature is described. Following selection of the target muscle sites, the apparatus supplies electrical muscle stimulation to each of the muscle sites to be contracted, on a alternating basis, the net effect of which is the muscle sites jointly apply a corrective force on a constant basis while, at the same time, each said muscle site has a rest period between each stimulation period. Each muscle site is not affected by the electrical stimulation of the other site. The apparatus has means for applying dual channel alternating stimulation pulses to target muscle sites, which pulses are overlapping during stimulation, and results in a constant force being applied on the curvature to be reduced without the muscle fatigue which would normally be associated with stimulation of a single muscle site on a constant basis.

4 Claims, 13 Drawing Figures

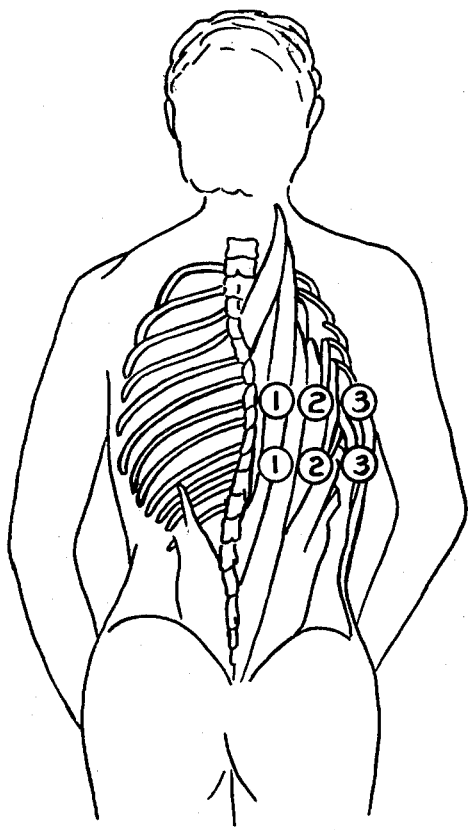
① MEDIAL
② INTERMEDIATE
③ LATERAL
Fig. 1
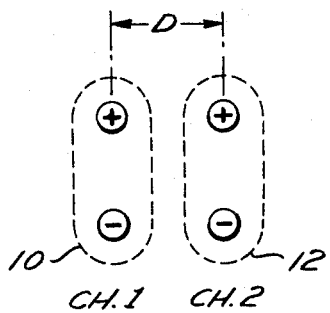
Fig. 2
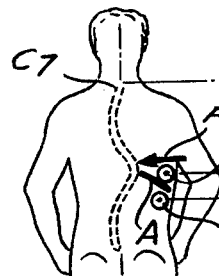 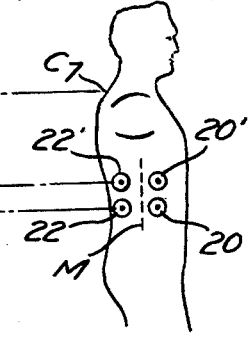
Fig. 3a (REAR VIEW)   Fig. 3b (SIDE VIEW)
A: APICAL RIB
M: MID AXILLARY LINE
S: SCOLIOTIC SPINE
F: CORRECTING FORCE GENERATED
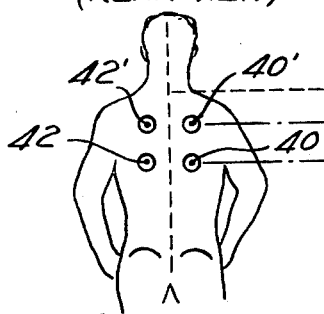 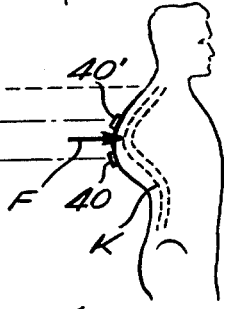
Fig. 4a (REAR VIEW)   Fig. 4b (SIDE VIEW)
K: KYPHOTIC SPINE (THORACIC)
F: CORRECTING FORCE GENERATED
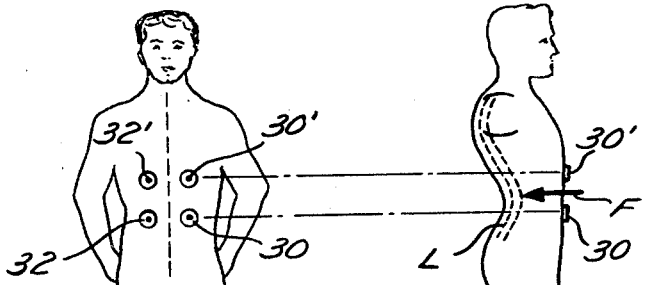
L: LORDOTIC SPINE (LUMBAR)
F: CORRECTING FORCE GENERATED
Fig. 5a (FRONT VIEW)   Fig. 5b (SIDE VIEW)

ELECTRICAL MUSCLE STIMULATION FOR TREATMENT OF SCOLIOSIS AND OTHER SPINAL DEFORMITIES

This application is a division of application Ser. No. 136,320, filed Apr. 1, 1980 now U.S. Pat. No. 4,342,317.

GOVERNMENTAL RIGHTS

The Government has rights in this invention pursuant to Contract No. RSA23P-55442/9 awarded by the Department of Health, Education and Welfare.

BACKGROUND OF THE INVENTION

Scoliosis, defined as lateral curvature of the spinal column, has in its mildest form an impact on cosmetic appearance alone, while severe scoliosis signifies deformity and cardiopulmonary impairment, remedial only by corrective spinal surgery, Initially, electrical stimulation through implanted electrodes appeared to be a feasible alternative to bracing in the treatment of progressive scoliosis in the growing child or teen-ager[1].

[1] Bobechko, W. P., Herbert, M.A.: Results of Using Electro-Spinal Instrumentation for the Treatment of Scoliosis at the Hospital for Sick Children, Toronto. Interim Report. Neuro-Rehabilitation Division, Medtronic, Inc., Oct. 1975.

Thereafter, this applicant has developed a clinical program for the treatment of idiopathic scoliosis using Lateral Electrical Surface Stimulation (LESS)[2,3,4,5] This included the design and production of a portable patient stimulator and the use of an appropriate surface electrode system.

[2] Rehabilitation Engineering Center at Rancho Los Amiogs Hospital, Annual Report of Progress, 1976, pp. 12-14.
[3] Axelgaard, J.: Scoliotic Curvature Induced by Electrical Stimulation. Final Project Report, Rehabilitation Engineering Center, Rancho Los Amigos Hospital, August, 1976.
[4] Rehabilitation Engineering Center at Rancho Los Amigos Hospital, Annual Report of Progress, 1977, pp. 12-15.
[5] Rehabilitation Engineering Center at Rancho Los Amigos Hospital, Annual Report of Progress, 1978, pp. 13-16.

Pending United States application Ser. No. 50,760 entitled "Transcutaneous Electrical Muscle Stimulation for Treatment of Scoliosis and Other Spinal Deformities" filed June 21, 1979 and now U.S. Pat. No. 4,326,534 is directed towards improvements in the reduction of scoliotic curvatures, and other spinal curvature deficiencies employing LESS, said application Ser. No. 50,760 and its teaching, being wholly incorporated herein by this reference.

A brief outline of the rationale for LESS methodology follows: a series of patients were first carefully screened for tolerance to surface electrical and stimulation optimum electrode location for the best acute curve correction [4, (infra)] Electrical Surface Stimulation (ESS) was applied through carbon impregnated silicone-rubber pads attached to a semi-solid conductive media (Ceptorpad TM) or coated with electrolytic gel (Spectra 360 TM) for a low impedance electrode-skin interfacing. Two of such electrodes were placed on the skin on the convex side of the curvature, symmetrically around the apex, in a medial (1) and two lateral locations [(2) intermediate, (3) full lateral] across the back (FIG. 1). A constant-current battery-operated generator supplied square wave pulses of 0.2 msec duration, 70 mA in amplitude, and at a rate of 30 pps. Duration of the wave pulses, amplitude and rate were all adjustable as set forth in the said pending application Ser. No. 50,760.

The ESS-screening results from a number of idopathic patients, proved that lateral electrode placement was the most effective configuration in acute curvature correction. On the average, the major stimulated curve corrected 2 degrees in the medial configuration* (3 cm lateral to the spinous processes), while the non-stimulated compensatory curve became 2 degrees worse. In the intermediate location, (2; FIG. 1 halfway between medial and lateral), the major curve improved 7 degrees and the minor curve improved 3 degrees. The lateral configuration (3; FIG. 1, electrodes on axillary line) exhibited 8 degrees of correction for the major stimulated curve while the compensatory curve corrected 4 degrees.
*FIG. 1,1

Based on the results of such ESS-screening, Lateral Electrical Surface Stimulation (LESS) appears to be the treatment of choice in the treatment of progressive scoliosis and other spinal curvature deficiencies.

In the preferred method of treatment, as set forth in detail in said patent application Ser. No. 50,760, LESS is applied during the hours of sleep only, with an ON-/OFF ratio of, for example 2:1 to 1:4 with OFF being five seconds or larger to prevent muscle fatigue. The LESS treatment follows that set forth, generally, above, i.e. the stimulating electrodes are placed symmetrically, about the reference center or apex of the major curvature to be reduced (in the thoracic area, the electrodes are placed about the apical rib as detailed in said Ser. No. 50,760, and in general, along the axillary line of the lateral muscles of the patient). The stimulus pulses applied to the selected muscle site are preferably DC compensated monophasic, (i.e. a zero net charge flows between electrodes) and have an amplitude of between about 60–80 mAmp, about 100-40 sec pulse width and about 20-30 pps. The details of the electrode placement, and electrical stimulation are more particularly set forth in said pending application Ser. No. 50,760.

The main objective of LESS treatment is not principally to strengthen the muscles being stimulated, but to cause asymmetrical pressures to be exerted on growth zones so as to effect a biomechanical straightening of the spine. Specifically, by applying lateral electrical stimulation to the surface of the skin, proximate specific trunk muscles, rather significant mechanical forces can be applied to the spine.

The reason why lateral muscle stimulation provides the most effective corrective force can readily be explained biomechanically. The medial, paraspinal muscles comprise a large muscle mass capable of generating large contraction forces when stimulated electrically, but the forces are mainly directed in a longitudinal direction which have only little effect on scoliotic curves because of the smaller lever arm of these muscles. On the other hand, when the smaller muscle mass of the lateral muscles are electrically stimulated, forces are produced which act on the ribs or ribs and pelvis, and strong moments are created which exert powerful lateral corrective forces on the spine.

It would seem quite clear that scoliosis correction would become more efficient by applying a constant force on the convexity of the scoliosis curvature. This approach implies a constant muscular contraction of muscle groups on the convexity of the curve. However, if the same muscle group is constantly stimulated, it will quickly fatigue and lose its developed tension. The invention herein provides a method and means of imparting a constant corrective force on the curvature to be reduced without causing the onset of muscle fatigue.

SUMMARY OF THE INVENTION

I have developed a method and means of stimulating two separate muscle sites or groups (surrounding the reference center or apex of the curvature to be reduced) in an alternating fashion whereby one muscle site contracts while the other relaxes and vice versa. In this method, one or the other of the muscle sites is always in a state of contraction so that a constant corrective force is being exerted[6]. However, because each muscle site is allowed to relax between contractions, a constant corrective force will be supplied without muscle fatigue.

[6] Axelgaard, J., Brown, J. C., Harada, Y., McNeal, D. R. and Nordwall, A.: Lateral Surface Stimulation for the Correction of Scoliosis. Presented at the Scoliosis Research Society Annual Meeting, Hong Kong, 1977. Abstract in Orthopaedic Transactions, J. Bone Joint Surg., 2:267, 1978.

The first step in the procedure is to select muscle sites which when contracted under pulsed electrical stimulation offers the greatest lever arm and moment of force for the reduction of the particular curvature involved. The optimal location of such target muscle sites or groups for treatment of various spinal deficiencies is now well known. For example, in the treatment of scoliosis, the stimulation target muscles lie in a band which stretches from the edge of the paraspinal muscles to the anterior axillary line; and preferably the most lateral electrode location on the mid axillary line or on the posterior axillary line is employed in the single channel electrical pulse wave stimulation technique described in pending application Ser. No. 50,760.

In the present method and means, the same stimulation target muscle groups or sites are employed as have been described in the pending application Ser. No. 50,760, but two pairs of electrodes, (each pair being connected to one channel of a dual-channel alternating electrical pulse wave generator) are carefully spaced on each of the two selected muscle sites or groups within the useful band of muscle so that no overlap of the stimulated muscle sites of contraction occurs when the dual-channel alternating stimulator is placed in operation.

The key to success following this methodology is that overlap of the two sites of muscle contraction must not occur. Because of the non-homogeneity of the stimulated medium (i.e., the body), it is difficult to predict which muscle groups are actually being stimulated and which are not.

To determine the size of the sites of muscle contraction, a logical approach would have been to use electromyograms (EMG's) to display the activity of the muscle during stimulation and, therefore, map out an area of stimulated muscle for a corresponding electrode stimulation site. This method, in actuality, does not appear to be technically feasible (due to recording amplifier saturation from the stimulation artifact) and/or is not practical because of the time involvement in the mapping out the total area of stimulation.

I have found that one superior method for the determination of non-overlapping stimulation areas is the use of thermography to delineate stimulated muscle sites.

Muscles produce heat, both in the resting state and when activated. Intrinsic heat production can be altered by local circulatory changes as well as environmental conditions.

Muscle work generates heat which transmits through the tissue and emits infrared electromagnetic radiation. Detection and registration of this infrared radiation from the body may be accomplished by a thermography camera which optically scans, in a matter of seconds, the area in question and focuses the image on an infrared detector. The detected image can then tranduce to electrical signals and be displayed on a video screen. The displayed thermogram may be hard-copied for later analysis.

Using the thermographic technique to locate muscle sites, I have found that application of alternating electrical pulse inputs, to each of two non-overlapping muscle sites, surrounding the reference center of the curvature to be reduced, cause constant corrective forces to be applied which appears, in many cases, to be substantially more useful in severe cases and/or more time efficient than the single channel ESS treatment methodology described in said application Ser. No. 50,760.

The methodology of the present application employs a dual-channel alternating stimulator wherein the ON-OFF times for each of the two channels are adjusted so that one muscle group starts to contract while the other starts to relax, and vice-versa. The ON-OFF cycling mode and electrical pulse pattern, including, RAMP-UP, HOLD and RAMP-DOWN of the pulse intensity (e.g., pulse width) in the ON portion, for each channel are within the same parameters as for the single channel ON-OFF cycling mode disclosed in said application Ser. No. 50,760.

From the clinical evidence available to date, indicating that the larger an external biomechanical corrective force (i.e., brace treatment and/or electrical stimulation) is applied the larger a curvature reduction can be expected, it appears that dual-channel alternating stimulation of non-overlapping muscle sites of contraction will result in greater curvature reduction of scoliotic curvatures and other types of spinal deformity curvatures - as compared with the use of a single channel stimulating means applied to a single muscle site (assuming conditions of the electrical pulse stimulation to be essentially equal on a per channel basis).

BRIEF DESCRIPTION OF DRAWINGS

FIG. 1 is a schematic, posterior-anterior (PA) view of the rib structure of a human being showing the medial, intermediate and lateral electrode positions in the ESS screening of a human being;

FIG. 2 is a representational view of a pair of stimulated electrodes emitting non-overlapping fields of stimulation of muscle sites;

FIGS. 3a and 3b are diagrammatic rear and side views, respectively showing electrode pair placements for a patient with thoracic scoliosis;

FIGS. 4a and 4b are diagrammatic rear and side views, respectively showing electrode pair placements for a patient with kyphosis;

FIGS. 5a and 5b are diagrammatic rear and side views, respectively showing electrode pair placements for a patient with lordosis;

DETAILED DESCRIPTION OF THE INVENTION

Figure 6A:
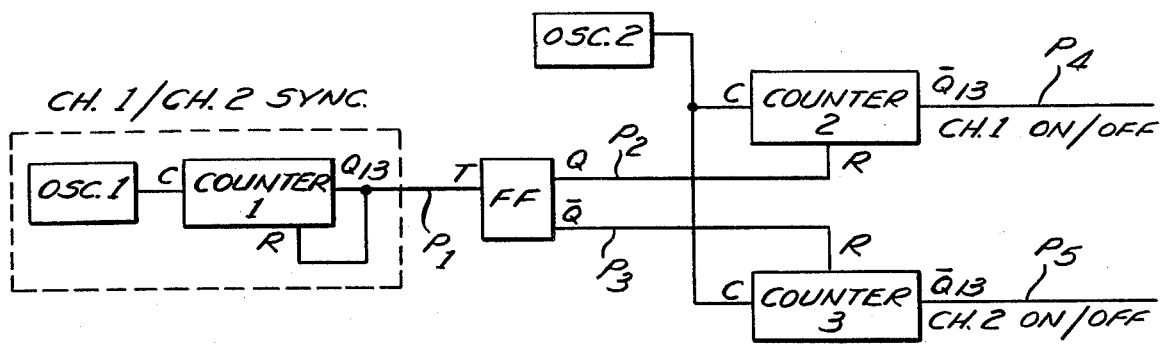
FIG. 6a is an electronic block diagram of a dual-channel alternating pulse generator and FIG. 6b is a series of wave forms generated by the pulse generator of FIG. 6a, FIGS. 7a and 7b are wave forms of channels 1 and 2 of a dual-channel alternating pulse generator showing the specific relationship between the ON-OFF portions of wave forms of each channel.

In carrying out the treatment process in accordance with the present invention, patients who have been diagnosed as suffering from scoliosis, lordosis, lordoscoliosis, kyphosis, or kyphoscoliosis, are initially screened to determine whether the transcutaneous electrical muscle stimulation method of treating the disease can be utilized. In carrying out the screening process, an AP (or PA) standing X-ray of the patient is taken for scoliosis, lateral standing X-ray for lordosis and kyposis, or AP (or PA) and lateral standing X-rays for lordoscoliosis and kyphoscoliosis, and measurements are made thereon to determine the location of the primary and compensatory curve(s) and to determine the degree of curvature of each (degrees determined by the Cobb measurement technique). By counting vertebrae on the patient's back, the apex is marked off by counting either from the $C_7$ vertebra in the neck iegion or from the $L_5$ vertebra in the lumbar region. The located apical vertebra then serves as the reference center in the placement of the stimulating electrodes. When the major curve to be treated is located in the thoracic area, the rib joining this apical vertebra becomes the reference center in the treatment of scoliosis, lordoscoliosis and lordosis. The location of the apical rib is palpated from the apical vertebra so the site of stimulation where the rib location is marked on the skin. If the curve to be corrected lies in the lumbar or thoracolumbar area, the reference center of the curve to be treated is the apical vertebra itself.

The target muscles to be stimulated are then selected. In the treatment of scoliosis the stimulation target muscles lie in a band which stretches from the edge of the paraspinal muscles to the anterior axillary line. The narrower band from the posterior axillary line to the anterior axillary line is preferred most often due to easiest electrode application and longest lever arm.

In the treatment of lordosis the stimulation target muscle groups are the rectus abdominis muscles bilateral to the anterior midline. Regional stimulation of the rectus abdominis at the spinal level of the apex of the lordotic curvature causes muscle contraction to flex the spine so that the curves correct. In the treatment of lordoscoliosis the stimulation target muscles at spinal levels associated symmetrically with the apex of the combined lordosis and scoliosis curves lie in the band between the anterior axillary line and the anterior midline.

In the treatment of kyphosis the stimulation target muscles are paraspinal musculature bilateral to the spinal processes. When the paraspinal musculature around the apex of the curvature is timulated into contraction the spinal processes and other posterior-lateral articulations are moved towards each other working as short levers for spinal extension and thereby kyphosis correction. In the treatment of kyphoscoliosis the stimulation target muscles are the unilateral paraspinal muscles on the convex side of the combined scoliosis and kyposis curve.

For the purpose of the following discussion, use of the terms "vertical" refer generally to the superior-inferior direction, and the term "transverse" refers generally to the direction perpendicular to superior-inferior.

Each of two pairs of stimulating electrodes are then placed in a symmetrical fashion above and below the reference center or apex of the curve to be treated, with the transverse distance between centers of the electrode pairs being temporarily set at a preliminary value of, for example, 10 cm, and the vertical distance between centers of electrode pairs being determined in accordance with the following guidelines:
  (a) a distance of 1 centimeter or less between electrode edges of each pair normally causes insufficient muscle contraction,
  (b) short curves of only few segments (3 to 5) or patients with short trunks normally require a distance between electrode edges of 2 to 4 centimeters,
  (c) based upon the most prevalent curve encountered, a distance of 5 centimeters between electrodes edges of each pair will normally suffice, and
  (d) long single curves (more than 7 segments) or patients with extremely long trunks will require a distance between electrode edges of each pair of from 6 to 11 centimeters.

Preferably, round electrodes 5 centimeters in diameter are used, but any electrode type of reasonable size and shape is acceptable. When round electrodes of 5 centimeters in diameter are utilized, the aforementioned distances between edges translate into the following distances between electrode centers:
  (a) 6 centimeters,
  (b) 7 to 9 centimeters,
  (c) 10 centimeters, and
  (d) 1 to 16 centimeters.

With the reference center and the vertical electrode distance selected for the curve(s) to be treated, the correct transverse distance between electrode pairs is determined according to the following guidelines:

After selection of the particular muscle group for the particular curve to be treated, a pair of specific muscle sites within the particular muscle group are selected such that the two muscle sites when stimulated by repititive electrical pulse inputs, on an alternating basis, must not result in any overlap of fields of stimulation.

The field of stimulation of a muscle site (under particular conditions of electrical muscle stimulation) is accurately and rapidly recorded by thermogrphic techniques (other techniques for mapping muscle site contraction may become available). In FIG. 2 areas of non-overlapping fields of stimulation 10, 12 set up by a dual-channel alternating stimulator, operating within preset parameters, is schematically shown. By way of example only, for electrical pulse generation on each channel of stimulation, on an alternating basis within the parameters set forth in application Ser. No. 50,760. The transverse distance between electrodes (distance D) lies generally between 6 and 20 cm, for treatment of lordosis curves, and between 6 and 15 cm for treatment of kyphosis curves.* The optimal distance between pairs of electrodes is readily ascertained for any particular patient by such thermographic techniques.

*and between 10 and 20 cm for scoliosis curves

Reference should now be made to FIGS. 3a, 3b wherein symmetrical placement of electrode pairs 20,20' and 22,22' about the mid-axillary line, for scoliotic curvature reduction is shown, by way of example. Reference should be made to FIGS. 4a, 4b wherein electrode pairs 40,40' and 42,42' are placed symmetrically on the paraspinal musculature about the posterior midline, for reduction of kyphosis curvatures; and reference should be made to FIGS. 5a, 5b wherein electrode pairs 30,30' and 32,32' are placed symmetrically on the rectus abdominis muscles. bilaterally about the anterior midline.

The locations where the electrode pairs are to be positioned are then marked with a semipermanent ink to facilitatelater electrode placement by the patient or a member of the patient's family. To keep the marks visible they would have to be touched up at regular intervals. The electrodes themselves are preferably round discs formed from a conductive rubber material, the discs being approximately five centimeters in diameter and having a snap-type connector to facilitate joining the electrode to a conductive lead. The connector must be a radiopaque material like metal to show up in the X-rays. The leads, in turn, are coupled to the output jacks or terminals of the stimulator. The electrodes are electrically coupled to the skin either via electrically conductive gel or an electrically conductive, flexible and adhesive disc shaped material. The electrodes and skin interface media may also be integrated into one self-contained unit.

The dual-channel alternating stimulator apparatus utilized to generate the desired alternating ON/OFF wave forms for each channel is shown, in block diagram form, in FIG. 6a. The oscillators (OSC1 and OSC2) and counters (counters 1, 2 and 3) in FIG. 6a may be of the type described in pending application Ser. No. 50,760, while the flip-flop (designated FF in FIG. 6a) is a JK type, for example RCA CMOS4027, converted into a type-T flip-flop, by conventional techniques. Counter 1 determines the synchronization (SYNC period) between the channels 1 and 2 and thereby the OFF-time. OSC1 is adjusted, by means described in pending application Ser. No. 50,760 to make the output $Q_{13}$ of the self-resetting counter 1 (because $Q_{13}$ is connected to R) go high at the beginning and middle of the ON/OFF waveform period. The type-T flip-flop (FF) resets counters 2 and 3 alternatingly of each other's SYNC pulse from the $Q_{13}$ output of counter 1. The ON-time of channel 1 and 2 is controlled by oscillator 2 (OSC2).

If R of counter 3 is connected to Q of the flip-flop (FF) in FIG. 6a instead of $\overline{Q}$, by means of a switch, the alternating dual channel waveforms will become synchronous dual channel. This mode is useful for simultaneous stimulatic of two curves as in a double-major scoliosis curvature configuration.

Figure 6B:
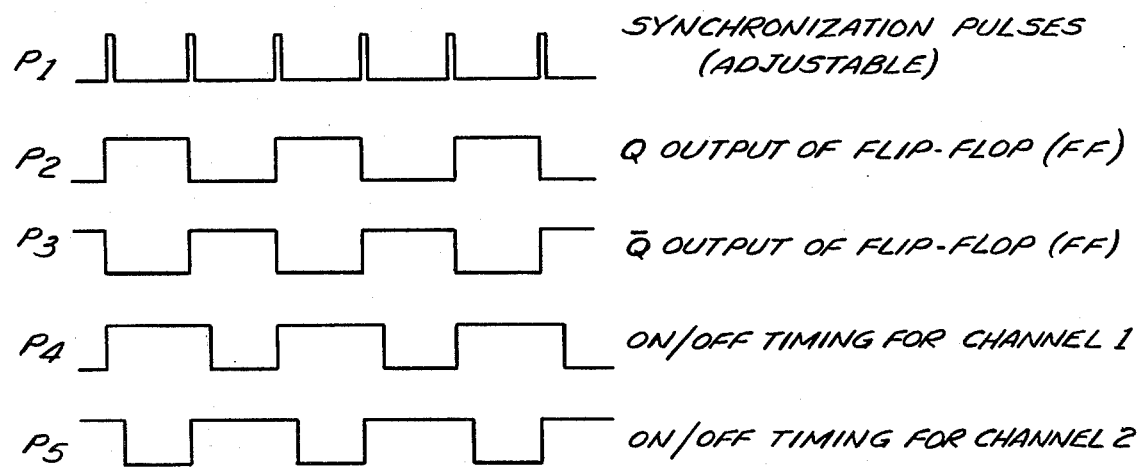
Figure 8:
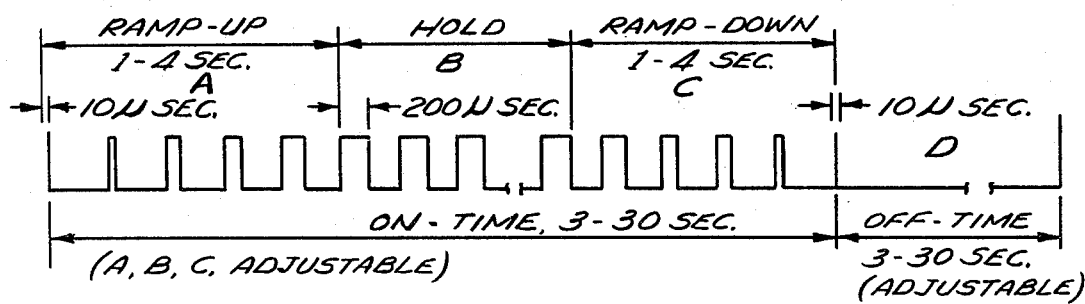
FIG. 8 is a more detailed showing of the ON portion of the pulse pattern of the output of channel 1 and channel 2 of FIGS. 7a or 7b.

The waveforms $P_1$ through $P_5$ generated at the various points shown in the schematic diagram of FIG. 6a are shown in FIG. 6b. The generation of the RAMP-UP, HOLD and RAMP-DOWN periods as well as the individual pulses produced during the ON-period are described in pending application Ser. No. 50,760 in detail, parameters of a particular waveform in the ON-period being shown in FIG. 8. Both channels are controlled by the same timing circuitry to assure similar output waveforms during the ON-period. The power output stages of channels 1 and 2, however, are two similar single channel output stages opto-isolated from each other and with separate battery supply voltage to prevent cross-over stimulation between electrode pairs of channels 1 and 2.

Figure 7A:
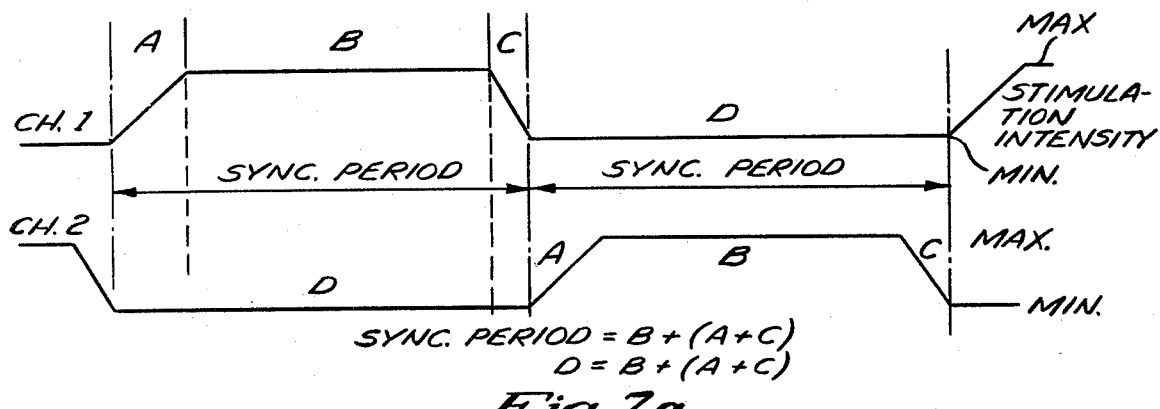
Figure 7B:
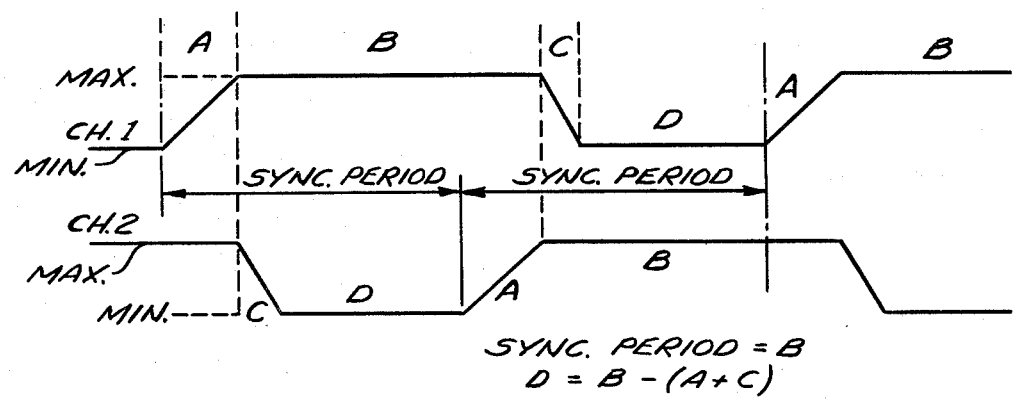

The alternating relationship of several combinations of final waveforms of channels 1 and 2 are seen in FIGS. 7a and 7b, the relationship being dictated by the synchronization period (SYNC period). In FIG. 7a the SYNC period is equal to the sum of the RAMP-UP (A) and HOLD (B) and RAMP-DOWN (C) portions of the ON phase of the pulse pattern. It will be noted that in FIG. 7a as the ON phase of channel 1 is RAMPED-DOWN, the ON phase of channel 2 commences to be RAMPED-UP so that the two muscle sites, in question, are being alternately contracted and relaxed but the constant force applied to the patient is being somewhat "cushioned" by virtue of RAMP-UP of channel 2 after RAMP-DOWN of channel 1. There is thus no overlap of RAMP-UP (A) and RAMP-DOWN (C) of channels 1 and 2. In FIG. 7b, the SYNC period is adjusted (shortened) so that RAMP-UP (A) of channel 2 to maximum intensity occurs before RAMP-DOWN (C) of channel 1 commences. This sequence may be employed where the patient can tolerate the full overlap of RAMP-UP (A) and RAMP-DOWN (C) phases between channels 1 and 2. In most applications, the variable SYNC period will be adjusted so that a partial overlap of the RAMP-UP (A) and RAMP-DOWN (B) portions of channels 1 and 2 will occur to assure a smooth transition between channels without fluctuations in spine curvature correctiveforces causing jitters of the spinal column.

By way of a specific example, in FIG. 7a the following time relationships for the pulse pattern are given:

RAMP-UP (A) = 2 seconds
HOLD (B) = 8 seconds
RAMP-DOWN (C) = 1 second
SYNC period = A + B + C = 11 seconds
D (OFF-period) = A + B + C = 11 seconds For FIG. 7b, the following time relationships are set forth, again merely by way of example:

RAMP-UP (A) = 2 seconds
HOLD (B) = 8 seconds
RAMP-DOWN (C) = 1 second
SYNC period = B (8 seconds) p1 D (OFF-period) = B − (A + C) = 5 seconds During the initial screening process, the amplitude is adjusted to produce suitable muscle contractions, but without causing the patient undue distress or discomfort. The patient is then advised to use the stimulator during an initial two-week familiarization and muscle conditioning phase, where the amplitude of stimulation is increased everyday according to the patient's increasing level of comfort. During the first week, the patient uses the dual-channel stimulator during daytime only according to the following schedule in order to prevent muscle fatigue:

Day 1-½ hour three separate times;
Day 2-1 hour two separate times;
Day 3-3 hours continuously;
Day 4-4 hours;
Day 5-5 hours;
Day 6-6 hours; and
Day 7-7 hours On the eighth day, the beginning of the second week, stimulation application is switched to night time while the patient sleeps. If less than eight hours of stimulation, supplementary daytime use is required. After two weeks of use, the patient will return to the physician's office where an examination will be made as to whether there is any noticeable skin irritation or other effects that may dictate changes of the treatment process. Possible skin irritation may be solved by the use of alternate skin interfacing materials.

Assuming that the patient does not exhibit any conditions which would preclude continued use of the method and apparatus, at the conclusion of the two-week familiarization phase, the clinician checks for correct electrode placement based on a prone X-ray of the entire spine with electrodes attached, but with no stimulation applied. In that the patient is now accustomed to the sensation of the electrical stimulation induced muscle contractions, an additional prone X-ray of the entire spine, with a fixed current amplitude of 70 mAmp for 4–5 seconds, is then taken. The curvature displayed in the X-rays are measured and compared. Improvement of the major curve and no worsening of the compensatory curve(s) must be seen in the X-ray taken with stimulation applied. If not, further electrode adjustment is necessary which may require further thermographic evaluation.

In utilizing the treatment method of the present invention, it is found that the amplitude of the stimulating pulses should be approximately 60–80 milliamperes, this value having been found to be a compromise between good muscle contractions and level of comfort. However, as described above in connection with the preferred stimulator design, the amplitude is adjustable so that greater or lesser stimulating currents may be utilized. The daily treatment time may be in the range of from about four hours to about sixteen hours per day.

At periodic intervals, e.g., three months, the patient is expected to return to the physician's office so that progress may be monitored. At the time of these visits, further X-rays may be taken to ensure that electrode placement is proper, that treatment of the major curve does not adversely affect the curvature of the compensatory curve and that the curve angle has not increased further.

It is believed that the foregoing dual-channel alternating stimulation method and means will be effective not only when the electrodes are mounted transcutaneously. but when the electrodes are mounted percutaneously or, in some cases, where the electrodes and associated pulse generating means is subcutaneously placed within the patient.

The invention has been described herein in considerable detail, in order to comply with the Patent Statutes and to provide those skilled in the art with information needed to apply the novel principles, and to construct and use any non-conventional components as required. However, it is to be understood that the invention can be carried out by specifically different equipment and devices, and that various modifications, both as to equipment details and operating procedures can be effected without departing from the spirit and scope of the invention itself.

I claim:

1. Apparatus for producing dual-channels of electrical pulse patterns for application to the patient by way of two pairs of body contacting electrodes to evoke separate fields of stimulation of predetermined muscle sites proximate the site of said pairs of electrodes, comprising:
   (a) means for repetitively applying a first selected electrical pulse pattern to one pair of said electrodes sufficient to evoke contraction and relaxation of one of said muscle sites;
   (b) means for applying a second selected electrical pattern to the other pair of said electrodes for contraction and relaxation of the other of said muscle sites;
   (c) each of said first and second electrical pulse patterns having a varable ON period and a variable OFF period, and each of said ON periods including a RAMP-up phase, a HOLD phase and a RAMP-DOWN phase; and
   (d) means for producing an adjustable synchronization pulse to trigger, in alternating fashion, the onset of said ON period of each of said first and second pulse patterns to produce, in alternate fashion, a partial overlap of said RAMP-UP and RAMP-DOWN phases of said first electrical pulse pattern with the ON period of said second electrical pulse pattern, and to produce non-simultaneous OFF periods in said first and second electrical pulse patterns, whereby each muscle site is placed, alternately, in a contraction and in a relaxation mode.

2. The apparatus of claim 1 wherein said synchronization pulse is variable and said variable ON period being at, or between:
   the sum of the time periods of said RAMP-UP, HOLD and RAMP-DOWN phases of said ON portion; and
   the time period of said HOLD phase.

3. The apparatus of claim 1 wherein said synchronization pulse triggers the onset of said ON period of one channel prior to completion of the RAMP-DOWN phase of said other channel whereby partial overlap of the ON periods of both channels occurs.

4. The apparatus of claim 2 wherein said synchronization pulse triggers the onset of said ON period of one channel prior to completion of the RAMP-DOWN phases of said other channel whereby partial overlap of the ON periods of both channels occurs.

* * * * *